US006274793B1

(12) United States Patent
Kobayashi et al.

(10) Patent No.: US 6,274,793 B1
(45) Date of Patent: Aug. 14, 2001

(54) INBRED BROCCOLI LINE 194-6-2CMS

(75) Inventors: Shigetoshi Kobayashi; Junichi Sasayama, both of Tsu; Toyokazu Akamatsu, Kakegawa, all of (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/361,212

(22) Filed: Jul. 27, 1999

(51) Int. Cl.[7] .............................. A01H 5/00; A01H 5/10; A01H 1/04; A01H 4/00
(52) U.S. Cl. ...................... 800/306; 800/300; 800/301; 800/302; 800/303; 435/410; 435/430
(58) Field of Search ........................ 800/306, 298, 800/260, 271, 274, 300, 301, 302, 303; 435/410, 430

*Primary Examiner*—Gary Benzion
*Assistant Examiner*—Melissa L. Kimball
(74) *Attorney, Agent, or Firm*—Rothwell, Figg, Ernst & Manbeck

(57) ABSTRACT

A novel broccoli cultivar, designated 194-6-2CMS, is disclosed. The invention relates to the seeds of broccoli cultivar 194-6-2CMS, to the plants of broccoli 194-6-2CMS and to methods for producing a broccoli plant produced by crossing the cultivar 194-6-2CMS with itself or another broccoli variety. The invention further relates to hybrid broccoli seeds and plants produced by crossing the cultivar 194-6-2CMS with another broccoli cultivar.

21 Claims, No Drawings

INBRED BROCCOLI LINE 194-6-2CMS

BACKGROUND OF THE INVENTION

The present invention relates to a new and distinctive broccoli cultivar, designated 194-6-2CMS. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher yield, resistance to diseases and insects, better stems and roots, tolerance to drought and heat, and better agronomic quality.

The cultivated plants associated with the species *Brassica oleracea* have been of great agricultural importance to mankind since ancient times. The introduction of hybrid cultivars to North America in the 1960's benefited the popularity of these crops by expanding the growing season, increasing yield and holding ability, and making large-scale production economically feasible. First generation ($F_1$) hybrid cultivars possess the advantage of genetic uniformity without the inbreeding depression inherent in true-breeding lines. Developing commercial Brassica hybrids requires the development of homozygous inbred parent lines. Homozygous inbred lines of broccoli can be develop by self-pollinating (selfing) for 8 to 9 generations or by deriving doubled haploid plants from anther culture.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

There are two primary objectives for commercial heading broccoli breeding programs. These are yield and plant shape. Yield is determined in units of harvested boxes per acre. The stem thickness of a broccoli cultivar is a significant component of yield. Optimum plant shape is characterized by a cultivar that is suitable for three markets: exportation of plant crowns (crown cut), processing of florets for food service and frozen product and bunching of stalks and large side shoots for fresh market produce markets. A third objective can be the development of heat tolerant cultivars. Such cultivars would possess flower primordia that are less susceptible to damage from high temperatures. Such cultivars could be grown in conditions where traditional broccoli types produce damaged, unacceptable heads.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior broccoli cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same broccoli traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new broccoli cultivars.

The development of new broccoli cultivars requires the development and selection of broccoli varieties, the crossing of these varieties and selection of superior hybrid crosses. The hybrid seed is produced by manual crosses between selected male-fertile parents or by using male sterility systems. Additional data on parental lines, as well as the phenotype of the hybrid, influence the breeder's decision whether to continue with the specific hybrid cross.

Many Brassica species have a genetic characteristic of self-incompatibility. Self-incompatibility (SI) is a genetic system that favors outcrossing and therefore maximizes recombination and variability in a species. Such variability is desirable in nature for wide adaptation and species survival. Self-incompatibility has been the most common form of pollination control in $F_1$ hybrid Brassica vegetables (Tsunoda et al., chapter 13). However, SI itself is not a satisfactory method for producing seed that is entirely or almost entirely hybrid. SI can breakdown at high temperatures and weakens at the end of a plant's reproductive stage. This can be extremely troublesome when the hybrid cross-pollination being produced uses parent lines that vary significantly. Problems such as achieving synchronous flowering between the two parent lines diminish the potential of SI to achieve high levels of hybridity. One example of such a cross-pollination is when cauliflower lines adapted to North American conditions are cross-pollinated with cauliflower lines adapted to tropical conditions.

Cytoplasmic male sterility (CMS) is another method used in Brassica vegetables species to produce $F_1$ hybrids. This method of producing hybrids is a more recent development in Brassica compared to self-incompatibility. A genetic mutation contained in the cytoplasm, more specifically the mitochondrial DNA, is responsible for the lack of production of functional pollen. In Brassica, the cytoplasm has commonly been identified in and transferred from "Ogura"-type radish (*Raphanus sativus*) (Ogura, 1968). The major advantage of CMS over self-incompatibility is that under normal conditions, no pollen is produced in the female parent. This results in the production of 100% hybrid seed. Under certain stressful growth conditions, however, it may be possible to produce small amounts of fertile pollen in CMS plants. Brassica inbreds containing CMS are maintained by continued hybridization to their normal (fertile) counterpart inbred, commonly referred to as a "B" line or a maintainer line.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

SUMMARY OF THE INVENTION

According to the invention, there is provided a novel broccoli cultivar, designated 194-6-2CMS. This invention thus relates to the seeds of broccoli cultivar 194-6-2CMS, to the plants of broccoli 194-6-2CMS and to methods for producing a broccoli plant by crossing the broccoli 194-6-2CMS with itself or another broccoli line.

Thus, any such methods using the broccoli variety 194-6-2CMS are part of this invention: selfing, backcrosses, hybrid production, crosses to populations, and the like. All plants produced using broccoli variety 194-6-2CMS as a parent are within the scope of this invention.

In another aspect, the present invention provides for single gene converted plants of 194-6-2CMS. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring broccoli gene or a transgene introduced through genetic engineering techniques.

In another aspect, the present invention provides regenerable cells for use in tissue culture of broccoli plant 194-6-2CMS. The tissue culture will preferably be capable of regenerating plants having the physiological and morphological characteristics of the foregoing broccoli plant, and of regenerating plants having substantially the same genotype as the foregoing broccoli plant. Preferably, the regenerable cells in such tissue cultures will be embryos, protoplasts, meristematic cells, callus, pollen, leaves, anthers, roots, root tips, flowers, seeds or stems. Still further, the present invention provides broccoli plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Plant Height: Plant height is measured in centimeters from the soil line to the top of the leaves.

Head Height: Head height is measured in centimeters from the soil line to the top of the head.

Head Diameter: Head Diameter is measured at the widest diameter of the head (from overhead) in centimeters.

Head Width: Head Width is measured in centimeters and is the diameter of the head at its widest point when viewed from above.

Head Length: Head Length is measured in centimeters from the top of the head to the lowest point of attachment to the stem of the florets that make the head.

Yield: The yield is the weight in grams for a harvested broccoli head or floret cluster.

Essentially all the physiological and morphological characteristics. A plant having essentially all the physiological and morphological characteristics means a plant having the physiological and morphological characteristics, except for the characteristics derived from the converted gene.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

DETAILED DESCRIPTION OF THE INVENTION

Broccoli cultivar 194-6-2CMS has superior characteristics and was developed by crossing 194-6-2 x MS-UL-1-6 $F_1$. This cross was then backcrossed to 194-6-2 five times.

Some of the criteria used to select in various generations include: seed yield, lodging resistance, emergence, disease tolerance, maturity, head shape, flower bud size, clean stem, heat tolerance and plant height.

It has been self-pollinated a sufficient number of generations with careful attention to uniformity of plant type. The line has been increased with continued observation for uniformity.

This invention is also directed to methods for producing a broccoli plant by crossing a first parent broccoli plant with a second parent broccoli plant, wherein the first or second broccoli plant is the broccoli plant from the line 194-6-2CMS. Further, both first and second parent broccoli plants may be from the cultivar 194-6-2CMS. Therefore, any methods using the cultivar 194-6-2CMS are part of this invention: selfing, backcrosses, hybrid breeding, and crosses to populations. Any plants produced using cultivar 194-6-2CMS as a parent are within the scope of this invention.

As used herein, the term "plant" includes plant cells, plant protoplasts, plant cells of tissue culture from which broccoli plants can be regenerated, plant calli, plant clumps, and plant cells that are intact in plants or parts of plants, such as pollen, flowers, embryos, ovules, seeds, beads, leaves, stems, roots, anthers and the like. Thus, another aspect of this invention is to provide for cells which upon growth and differentiation produce a cultivar having essentially all of the physiological and morphological characteristics of 194-6-2CMS.

Culture for expressing desired structural genes and cultured cells are known in the art. Also as known in the art, broccoli is transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich, et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in Methods in Plant Molecular Biology & Biotechnology, Glich, et al., (Eds. pp. 67–88 CRC Press, 1993); and by Phillips, et al., "Cell-Tissue Culture and In-Vitro Manipulation" in Corn & Corn Improvement, 3rd Edition; Sprague, et al., (Eds. pp. 345–387) American Society of Agronomy Inc., 1988. Methods of introducing expression vectors into plant tissue include the direct infection or co-cultivation of plant cells with *Agrobacterium tumefaciens*, Horsch et al., Science, 227:1229 (1985). Descriptions of Agrobacterium vectors systems and methods for Agrobacterium-mediated gene transfer provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device Agrobacterium-medicated transformation. Transformant plants obtained with the protoplasm of the invention are intended to be within the scope of this invention.

The present invention contemplates a broccoli plant regenerated from a tissue culture of a variety (i.e., 194-6-2CMS) or hybrid plant of the present invention. As is well known in the art, tissue culture of broccoli can be used for the in vitro regeneration of a broccoli plant. Tissue culture of various tissues of broccoli and regeneration of plants therefrom is well known and widely published. Thus, another aspect of this invention is to provide cells which upon growth and differentiation produce broccoli plants having the physiological and morphological characteristics of variety 194-6-2CMS.

The cultivar 194-6-2CMS is similar to 194-6-2. While similar to 194-6-2, there are numerous differences including 194-6-2CMS does not produce functional pollen.

TABLES

Table 1 below shows the improvement in hybridity level possible after 194-6-2CMS was developed through backcrossing. As shown in Table 1 (columns 1–3), from 1993 to 1996 different attempts were made at producing H669 x 194-6-2. None of the 15 sized seed lots from these productions yielded seed with hybridity levels above ninety percent. As shown in columns 4–6 of Table 1, seed productions with hybridity levels above 99% were routinely produced using 194-6-2CMS.

TABLE 1

| H669 x 194-6-2 | | | 194-6-2CMS x H669 | | |
|---|---|---|---|---|---|
| Year | Lot | Hybridity % | Year | Lot | Hybridity % |
| 1993 | 155141 | 87.3 | 1997 | 194612 | 99.9 |
|  | 155142 | 85.3 |  | 194613 | 99.9 |
|  | 155143 | 71.1 |  | 194614 | 99.9 |
| 1993 | 155151 | 65.3 |  | 194615 | 99.9 |
|  | 155152 | 31.3 | 1997 | 198071 | 99.9 |
|  | 155153 | 15.3 |  | 198072 | 99.3 |
| 1994 | 161341 | 87.3 |  | 198073 | 98.7 |
|  | 161342 | 82.7 |  | 198074 | 98.7 |
|  | 161343 | 79.3 |  | 198075 | 99.3 |
| 1994 | 164181 | 67.3 |  |  |  |
|  | 164182 | 28.0 |  |  |  |
|  | 164183 | 50.7 |  |  |  |
| 1996 | 187061 | 91.4 |  |  |  |
|  | 187062 | 88.0 |  |  |  |
|  | 187063 | 64.0 |  |  |  |

Table 2 shows weight, width and length of the head dimensions of 3 broccoli hybrids. As shown in Table 2, the heads from a hybrid between 194-6-2CMS and a broccoli inbred H669 are smaller in head weight and head width and longer in length than the heads of broccoli hybrids Patriot and Greenbelt. The 194-6-2CMS x H669 cross results in a product similar to regular broccoli, but possessing a longer, slender appearance. The hybrid of the present invention produces a length to width ratio more than twice that of typical broccoli hybrids.

TABLE 2

| 194-6-2CMS x H669 | | | Hybrid Broccoli Patriot | | | Hybrid Broccoli Greenbelt | | |
|---|---|---|---|---|---|---|---|---|
| Head Weight (g) | Head Width (cm) | Head Length (cm) | Head Weight (g) | Head Width (cm) | Head Length (cm) | Head Weight (g) | Head Width (cm) | Head Length (cm) |
| 90 | 10 | 16.5 | 176 | 11 | 12 | 200 | 11.5 | 10 |
| 77 | 9 | 18 | 151 | 10.5 | 11 | 179 | 11.5 | 11 |
| 52 | 6 | 17 | 193 | 11.5 | 12.5 | 142 | 11 | 11 |
| 83 | 7.5 | 18.5 | 217 | 11 | 14 | 243 | 13 | 13 |
| 68 | 9 | 17 | 135 | 10.5 | 11 | 192 | 10 | 10 |
| 116 | 8 | 20.5 | 251 | 13 | 14 | 185 | 10.5 | 11 |
| | | | | MEAN | | | | |
| 81.0 | 8.35 | 17.92 | 187.17 | 11.25 | 12.42 | 190.17 | 11.25 | 11.0 |

When the term broccoli plant is used in the context of the present invention, this also includes any single gene conversions of that inbred or variety. The term single gene converted plant as used herein refers to those broccoli plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term backcrossing as used herein refers to the repeated crossing of a hybrid progeny back to the recurrent parent. The parental broccoli plant which contributes the gene for the desired characteristic is termed the nonrecurrent or donor parent. This terminology refers to the fact that the nonrecurrent parent is used one time in the backcross protocol and therefore does not recur. The parental broccoli plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a broccoli plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus.

DEPOSIT INFORMATION

A deposit of the broccoli seed of this invention was made with the American Type Culture Collection, Manassas, Va. on Sep. 21, 1999 having ATCC designation number PTA-735.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A broccoli seed designated 194-6-2CMS, wherein a sample of said seed has been deposited under ATCC Accession No. PTA-735.

2. A plant, or its parts, produced by growing the seed of claim 1.

3. Pollen of the plant of claim 2.

4. An ovule of the plant of claim 2.

5. A broccoli plant, or parts thereof, having all of the physiological and morphological characteristics of the broccoli plant of claim 2.

6. Tissue culture of the seed of claim 1.

7. A broccoli plant regenerated from the tissue culture of claim 6, wherein said broccoli plant is capable of expressing all the physiological and morphological characteristics of inbred broccoli line 194-6-2CMS.

8. Tissue culture of regenerable cells of the plant, or its parts, of claim 2.

9. The tissue culture of claim 8 wherein the regenerable cells are embryos, meristematic cells, pollen, leaves, anthers, roots, root tips, flowers, seeds, stems, beads, or protoplasts or calli derived therefrom.

10. A broccoli plant regenerated from the tissue culture of claim 9, wherein said broccoli plant is capable of expressing all the physiological and morphological characteristics of inbred broccoli line 194-6-2CMS.

11. A method for producing a broccoli seed comprising crossing a first parent broccoli plant with a second parent broccoli plant and harvesting the resultant hybrid broccoli seed, wherein said first or second parent broccoli plant is the broccoli plant of claim 2.

12. A hybrid broccoli seed produced by the method of claim 11.

13. A hybrid broccoli plant, or its parts, produced by growing said hybrid broccoli seed of claim 12.

14. The broccoli plant, or its parts, of claim 5, further comprising a single gene conversion.

15. The single gene conversion broccoli plant of claim 14, wherein the gene is a gene which is introduced by transgenic methods.

16. The single gene conversion broccoli plant of claim 14, wherein the gene is a dominant allele.

17. The single gene conversion broccoli plant of claim 14, wherein the gene is a recessive allele.

18. The single gene conversion broccoli plant of claim 14, wherein the gene confers herbicide resistance.

19. The single gene conversion broccoli plant of claim 14, wherein the gene confers insect resistance.

20. The single gene conversion broccoli plant of claim 14, wherein the gene confers resistance to bacterial, fungal or viral disease.

21. The single gene conversion broccoli plant of claim 14, wherein the gene confers male sterility.

* * * * *